(12) United States Patent
Silverman et al.

(10) Patent No.: US 8,618,143 B1
(45) Date of Patent: Dec. 31, 2013

(54) SELECTIVE NEURONAL NITRIC OXIDE SYNTHASE INHIBITORS WITH AZOLE SUBSTITUENTS

(75) Inventors: Richard B. Silverman, Northbrook, IL (US); James M. Kraus, Chicago, IL (US)

(73) Assignee: Northwestern University, Evanston, IL (US)

( * ) Notice: Subject to any disclaimer, the term of this patent is extended or adjusted under 35 U.S.C. 154(b) by 140 days.

(21) Appl. No.: 13/275,748

(22) Filed: Oct. 18, 2011

Related U.S. Application Data

(60) Provisional application No. 61/394,150, filed on Oct. 18, 2010.

(51) Int. Cl.
| | | |
|---|---|---|
| *A61K 31/44* | (2006.01) | |
| *A61K 31/40* | (2006.01) | |
| *C07D 213/70* | (2006.01) | |
| *C07D 207/00* | (2006.01) | |

(52) U.S. Cl.
USPC ............ 514/357; 514/428; 546/311; 548/544

(58) Field of Classification Search
USPC ................... 514/357, 428; 546/311; 548/544
See application file for complete search history.

(56) References Cited

U.S. PATENT DOCUMENTS

| 7,470,790 B2 | 12/2008 | Silverman et al. |
| 7,994,326 B2 | 8/2011 | Silverman et al. |
| 2010/0292484 A1 | 11/2010 | Silverman et al. |

OTHER PUBLICATIONS

Bergmeier, S. and Stanchina D., "Synthesis of Vicinal Amino Alcohols via a Tandem Acylnitrene Aziridination—Aziridine Ring Opening", J. Org. Chem. 1997, 62, 4449-4456.
Correia, M.A. and Ortiz de Montellano, P.R., "Inhibition of Cytochrome P450 Enzymes", Cytochrome P450: Structure, Mechanism and Biochemistry, 3e, Kluwer Academic / Plenum Publishers, New York, 2005.
Ji, H.; Li, H.; Flinspach, M.; Poulos, T.; Silverman, R., "Computer Modeling of Selective Regions in the Active Site of Nitric Oxide Synthases: Implication for the Design of Isoform-Selective Inhibitors", J. Med. Chem. 2003, 46, 5700-5711.
Ji, H.; Stanton, B.; Igarashi, J.; Li, H.; Martasek, P.; Roman, L.; Poulos, T.; Silverman, R., "Minimal Pharmacophoric Elements and Fragment Hopping, an Approach Directed at Molecular Diversity and Isozyme Selectivity. Design of Selective Neuronal Nitric Oxide Synthase Inhibitors", J. Am. Chem. Soc. 2008, 130, 3900-3914.
Ji, H.; Tan, S.; Igarashi, J.; Li, H.; Derrick, M.; Martasek, P.; Roman, L.; Vasquez-Vivar, J.; Poulos, T.; Silverman, R., "Selective Neuronal Nitric Oxide Synthase Inhibitors and the Prevention of Cerebral Palsy", Ann Neurol 2009; 65: 209-217.
Kraus, J.; Verlinde, C.; Karimi, M.; Lepesheva, G.; Gelb, M.; Buckner, F., "Rational Modification of a Candidate Cancer Drug for Use Against Chagas Disease", J. Med. Chem. 2009, 52, 1639-1647.
Moore, P. and Handy, R., "Selective Inhibitors of Neuronal Nitric Oxide Synthase—is no NOS Really Good NOS for the Nervous System?", Trends in Pharmaceutical Science, Jun. 1997, vol. 18.
Silverman, Richard B. "Design of Selective Neuronal Nitric Oxide Synthase Inhibitors for the Prevention and Treatment of Neurodegenerative Diseases", Accounts of Chemical Research, vol. 42, Mar. 2009, 439-451.
Silverman et al. U.S. Appl. No. 13/250,554, filed Sep. 30, 2011.

*Primary Examiner* — Paul Zarek
(74) *Attorney, Agent, or Firm* — Reinhart Boerner Van Deuren s.c.

(57) ABSTRACT

Non-peptide, azole-substituted nitric oxide snythase inhibitor compounds, compositions and related methods, as can be used to enhance bioavailability and inhibit production of nitric oxide.

19 Claims, 2 Drawing Sheets

SELECTIVE NEURONAL NITRIC OXIDE SYNTHASE INHIBITORS WITH AZOLE SUBSTITUENTS

This application claims priority benefit of application Ser. No. 61/394,150 filed Oct. 18, 2010, the entirety of which is incorporated herein by reference.

BACKGROUND OF THE INVENTION

Nitric oxide synthase (NOS) is a heme-dependent monooxygenase that catalyzes the conversion of L-arginine to L-citrulline, producing nitric oxide (NO), through a five electron process involving oxidative removal of the imine nitrogen of the guanidino moiety of endogenous L-arginine. The active form of the enzyme is a homodimer, which requires flavin, heme, NADPH, and tetrahydrobiopterin prosthetic groups. (See, Moore, P. K.; Handy, R. L. C. Selective Inhibitors of Neuronal Nitric Oxide Synthase-Is No NOS Really Good NOS for the Nervous System? *Trends in Pharmaceutical Science* 1997, 18, 204-211.) Three isoforms of NOS are known: a form found in the brain and mitochondria (nNOS), a form found in the endothelium (eNOS), and an inducible form expressed during immune system response (iNOS). All three isoforms use the same substrate. Under normal circumstances, NO is an important second messenger, activating the formation of cyclic guanosine 3',5'-monophosphate (cGMP).

Oxidative stress caused by excess NO has been implicated in the pathogenesis of certain neurodegenerative diseases, including cerebral palsy and Parkinson's disease (PD). In both diseases, high levels of NO are implicated in the degeneration of neurological tissues. In the case of cerebral palsy, a mechanical complication during the birthing process can lead to low oxygen levels in the fetal brain—causing cell membrane depolarization due to energy starvation, which in turn floods the cells with calcium. NOS is also activated—producing excess NO, which is toxic for mitochondria and leads to apoptosis. Excess NO is linked to the progression of PD on several fronts, such as protein aggregation due to nitrative modification and misfolding, disruption of systems involved in degradation and clearance of aberrant proteins, as well as inactivation of regulatory mechanisms of cell death pathways.

It is believed that selective inhibition of nNOS under pathological conditions could be neuroprotective. (Ji, H.; Tan, S.; Igarashi, J.; Li, H.; Derrick, M.; Martasek, P.; Roman, L. J.; Vasquez-Vivar, J.; Poulos, T. L.; Silverman, R. B., Selective Neuronal Nitric Oxide Synthase Inhibitors and the prevention of Cerebral Palsy, *Ann. Neurol.* 2008, 64, 1-9.) It is also understood that eNOS is involved in vasoconstriction, which mediates blood pressure. The structures of both isoforms are very similar. Therefore, any therapeutic benefit resulting from non-selective NOS inhibition is counter balanced by a dangerous increase in blood pressure. Accordingly, the search for a selective inhibitor of nNOS has been ongoing in the art.

SUMMARY OF THE INVENTION

In light of the foregoing, it is an object of the present invention to provide compounds and related methods of use, generally, for the inhibition of nitric oxide synthase, and more specifically, for the selective inhibition of the neuronal isoform—thereby overcoming various deficiencies and shortcomings of the prior art, including those outlined above. It will be understood by those skilled in the art that one or more aspects of this invention can meet certain objectives, while one or more other aspects can meet certain other objectives. Each objective may not apply equally, in all its respects, to every aspect of this invention. As such, the following objects can be viewed in the alternative with respect to any one aspect of this invention.

It can be another object of the present invention to provide one or more NOS inhibitor compounds exhibiting sufficient lipophilicity to penetrate cellular membranes and/or the brain blood barrier, while preferably maintaining potency and selectivity for the neuronal isoform.

It can be an object of the present invention to provide one or more small molecule and/or non-peptide compounds exhibiting selective nNOS inhibition, over other enzyme isoforms.

It can be an object of the present invention to provide one or more with such non-peptide compounds for use and study under conditions promoting nitric oxide production, such conditions indicative of one or more mammalian disease states.

It can be an object of the present invention, alone or in conjunction with one or more of the preceding objectives, to provide one or more such compounds or corresponding pharmaceutical compositions enabling in vivo treatment of such mammalian disease states, such compounds as can be used to enhance penetration through biomembranes—in particular, the blood brain barrier—and/or to increase the bioavailability of such compounds.

Other objects, features, benefits and advantages of the present invention will be apparent from this summary and its descriptions of certain embodiments of such compounds, and will be readily apparent to those skilled in the art having knowledge of the synthetic techniques described therewith. Such objects, features, benefits and advantages will be apparent from the above as taken into conjunction with the accompanying examples, data, figures and all reasonable inferences to be drawn therefrom.

In part, the present invention can be directed to compounds of a formula

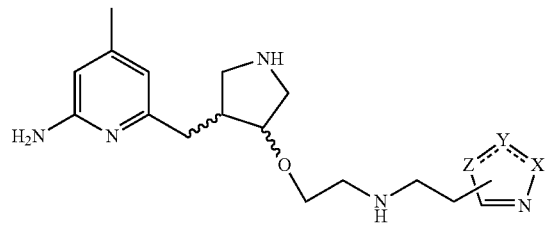

wherein X, Y and Z can be independently selected from $CR_1$, $CH_2$ and a heteroatom (e.g., from N, O and S) or related heteroatom moieties (e.g., $NR_2$), providing proper valence considerations; $R_1$ can be independently selected from H, alkyl (e.g., without limitation, $C_1$-about $C_4$) and halo (e.g., moieties and a covalent bond to said ethanamine moiety); and $R_2$ can be independently selected from H and alkyl (e.g., without limitation, $C_1$-about $C_4$) moieties and a covalent bond to said ethanamine moiety. As would be understood by those skilled in the art, such an azolyl moiety—depending on selection of X, Y and Z—can be linked to such a compound at any position relative to the azolyl nitrogen. Such a compound can be present as a salt, hydrate and/or solvate thereof and, optionally, in a pharmaceutical composition comprising one or more such compounds and, optionally, a pharmaceutically-acceptable carrier.

The structure of such a compound is limited only by a choice of starting material or reagent, in accordance with synthetic procedures of the sort described herein. Likewise, generally, X, Y and Z are limited only by the resulting azolyl moiety and heme coordination with or binding effect on a nitric oxide synthase. Alternatively, such azolyl moieties can be considered in the context of basicity, protonation and resulting degree of molecular positive charge at physiological pH. Accordingly, it will be understood by those skilled in the art that compounds of this invention can be present as an acid salt. Without limitation, certain embodiments can be partially or fully protonated to provide the corresponding ammonium salt, whereby the counter ion(s) can be a conjugate base (e.g., chloride) of a protic (e.g., hydrochloric) acid.

In certain non-limiting embodiments, each of X and Z can be CH, and Y can be NH, such that a corresponding compound can comprise an imidazolyl moiety. Alternatively, in various other non-limiting embodiments, each of X and Y can be CH, and Z can be S, such that a corresponding compound can comprise an thiazolyl moiety. Regardless, with respect to broader aspects of this invention, the present compounds are without stereochemical limitation. Where such compounds and/or their intermediates are available as racemic mixtures, the respective isomers can be resolved. Likewise, as such compounds are diastereomers, the corresponding enantiomers can be separated. Accordingly, any such stereocenter can be (S) or (R), with respect to any other stereocenter(s), whether such a compound is present as a salt, hydrate and/or solvate thereof. Such a compound can be selected from the cis, (S,S) or (R,R), enantiomers. Without limitation, the (R,R) enantiomer can be utilized to configure the azolyl moiety of such a compound for heme coordination upon NOS contact.

In part, the present invention can also be directed to a neuronal nitric oxide synthase inhibitor compound of the formula

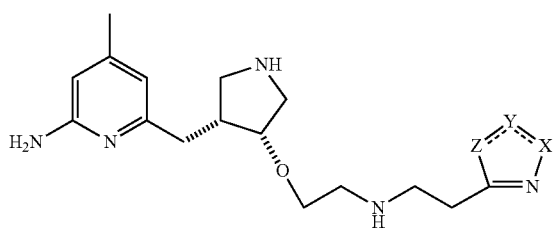

wherein X, Y and Z can be independently selected, as described above, from $CR_1$, $CH_2$ and a heteroatom or related heteroatom moiety (e.g., $NR_2$), providing proper valence consideration; $R_1$ can be independently selected from H, alkyl (e.g., without limitation, $C_1$-about $C_4$) and halo (e.g., fluoro, chloro, etc.) moieties; and $R_2$ can be independently selected from H and alkyl (e.g., without limitation, $C_1$-about $C_4$) moieties. In certain non-limiting embodiments, such an azolyl moiety can be selected from various imidazolyl (e.g., imidazol-4-yl), oxazolyl (e.g., oxazol-2-yl) and thiazolyl (e.g., thiazol-2-yl) moieties. As discussed above, such compounds are not restricted by either charge or stereochemistry, and can be present as a salt, hydrate and/or solvate thereof whether or not part of pharmaceutical composition.

While the present invention is illustrated in the context of a 4-methyl pyridine moiety conjugated with a pyrrolidine core, it will be understood by those skilled in the art that such compounds can be prepared to provide various other pyridine and other heterocyclic moieties. For example, without limitation, various other heterocyclic moieties including but not limited to substituted and unsubstituted thiazine, oxazine, pyrazine, oxazole and imidazole moieties and various other pyrrolidine and other heterocyclic moieties including but not limited to piperidine, tetrahydrofuran, tetrahydrothiophen, etc.—regardless of the presence or protection of an amino substituent—are described in U.S. Pat. No. 7,470,790 issued Dec. 30, 2008 and co-pending application Ser. No. 11/906,283 filed Oct. 1, 2007, in the context of substructures I and II as discussed more fully therein, each of which is incorporated herein by reference in its entirety. Regardless, where applicable, corresponding chiral pyrrolidine core compounds can be prepared, for instance, using synthetic techniques of the sort described herein or in co-pending application Ser. No. 12/781,139 filed May 17, 2010—the entirety of which is incorporated herein by reference, or straight forward modifications thereof, as would be understood by those skilled in the art and made aware of this invention. Such heterocycle-conjugated compounds can be used en route to selective nNOS inhibitors of the sort described in the aforementioned incorporated references.

In part, the present invention can be directed to a method of using azolyl basicity to affect bioavailability of a nitric oxide synthase inhibitor compound. Such a method can comprise providing a compound of the sort described herein, such a compound as can comprise an azolyl moiety with an imine nitrogen substantially unprotonated at physiological pH; and contacting such a compound with a lipophilic medium. Bioavailability can be assessed by one or more enzyme or cell-based assays of the sort understood by those skilled in the art, and corresponding inhibition of nitric oxide production indicating membrane permeability and effective compound cellular concentration. In certain non-limiting embodiments, such an azolyl moiety can have a $pK_a$ value ≤ about 5.4. More generally, such moieties are limited only by substantial lack of contribution to overall molecular positive charge at physiological pH. Regardless, such a medium can be in vivo or, alternatively, can model either a cellular membrane or a brain blood barrier.

In part, the present invention can also provide a method of inhibiting nitric oxide synthase. Such a method can comprise contacting, whether in vitro or in vivo, a nitric oxide synthase with an effective amount of any one or more of the present compounds or compositions, including but not limited to those illustrated by the following examples, referenced figures and/or accompanying synthetic schemes. More specifically, as also supported herein, the present invention can provide a method for selective inhibition of neuronal nitric oxide synthase. In certain such embodiments, as demonstrated below, such contact or administration to a mammalian subject can selectively inhibit neuronal nitric oxide synthase over inducible and endothelial isoforms. Regardless, such a compound can be selected from the (S,S) and (R,R) enantiomers and, without limitation, a corresponding azolyl moiety can be selected from imidazolyl and thiazolyl moieties. In certain such embodiments, the (R,R) enantiomer can be utilized for selective inhibition of neuronal nitric oxide synthase.

DETAILED DESCRIPTION OF CERTAIN EMBODIMENTS

Figure 1:
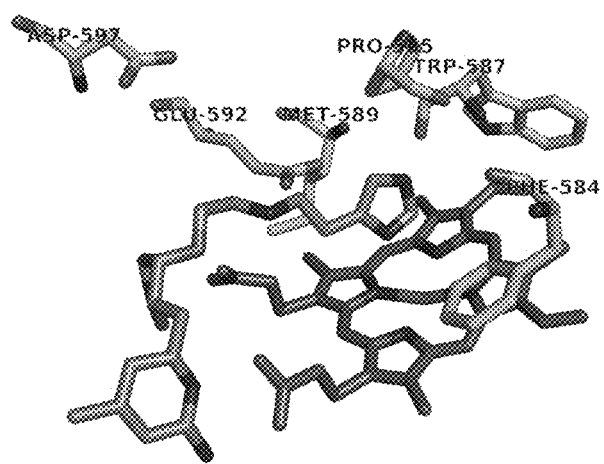
FIG. 1. Schematic illustration of heme coordination of an imidazolyl moiety, in accordance with non-limiting compounds and methods of the present invention.

As relates to the development of certain embodiments of this invention, a fragment-based de novo computer design methodology called "fragment hopping" has been used to identify the minimal pharmacophoric elements to relate structure and chemical properties with selectivity. (See, e.g., Ji, H.; Li, H.; Flinspach, M.; Poulos, T. L.; Silverman, R. B. Computer Modeling of Selective Regions in the Active Site of Nitric Oxide Synthases Implication for the Design of Isoform-Selective Inhibitors. *J. Med. Chem.* 2003, 46, 5700-5711; Ji, H.; Stanton, B. Z.; Igarashi, J.; Li, H.; Martsek, P.; Roman, L. J.; Poulos, T. L.; Silverman, R. B. Minimal Pharmacophoric Elements and Fragment Hopping, and Approach Directed at Molecular Diversity and Isozyme Selectivity. Design of Selective Neuronal Nitric Oxide Synthase Inhibitors. *J. Am. Chem. Soc.* 2008, 130, 3900-3914.) This methodology led to the discovery of a first non-peptidic nNOS selective inhibitor, compound 1.

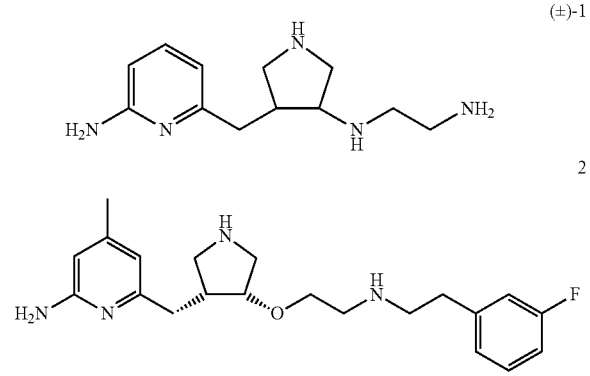

Racemic compound 1 has a $K_i$ of 388 nM against nNOS and a $K_i$ of 434.5 µM and 58.4 µM against eNOS and iNOS, respectively—providing an nNOS/eNOS selectivity of more than 1000 fold and a nNOS/iNOS selectivity of around 150 fold. Based on the crystal structure with 1 bound, a hydrophobic moiety was added to enhance potency, and the NH adjacent to the pyrrolidine ring was changed to an O to increase blood brain barrier penetration. Such considerations suggested the racemate of 2, which had further improved selectivity relative to 1 and a $K_i$ against nNOS of 5 nM.

Resolution of the enantiomers of 2 led to an unexpected result. A nNOS/2 co-crystal structure revealed that one enantiomer of 2 had a 180° reverse binding mode from that predicted by computer modeling. Examination of the crystal structure reveals that the 3-fluorophenyl ring is oriented above the heme and appears to be involved in pi-stacking. Displacement of the sixth ligand (water) from heme without iron coordination leads to a shift away from planarity of the iron-porphyrin complex.

Despite the unexpected binding mode, 2 was the most selective nNOS inhibitor. At the same time, the fact that the 3-fluorophenyl ring is directly adjacent to the heme ring, presented an opportunity to achieve improved potency. It was reasoned that as the 3-fluorophenyl ring does not afford any specific interactions beyond pi-stacking interactions with the heme, it should not be required for selectivity. Further, if the substituent located at this position, proximal to the heme ring, were to be substituted for a moiety that could coordinate to the iron atom, it would anchor the inhibitor compound in this binding mode and simultaneously be expected to dramatically increase potency.

With the co-crystal structure of compound 2 and the target enzyme already solved, the binding mode is known. It was speculated that if the iron were to be targeted for coordination, the design of an iron-coordinating compound could be derived from the crystal structure of 2, with computer modeling suggesting modifications to the structure of 2 in its current binding mode. Without other structural change, modification of ring and side chain were considered to put the iron coordinating moiety at a productive distance and orientation for coordination with the heme.

One such ring substitution is a C-4 linked imidazole. The structure of 2 was modified, then minimized in the active site using the Sybyl Force Field in Sybyl 8.1 molecular modeling software. The torsional angle of the imidazole was adjusted slightly to obtain the optimum angle for heme coordination. Simulated substitution for C-4 linked imidazole revealed that an ethyl linker (unchanged from the linker attaching the phenyl ring in compound 2) should allow the imidazole moiety to coordinate to the heme (FIG. 1). The images were generated using PyMol Molecular Graphics System by DeLano Scientific, Palo Alto, Calif., USA.

Figure 2:
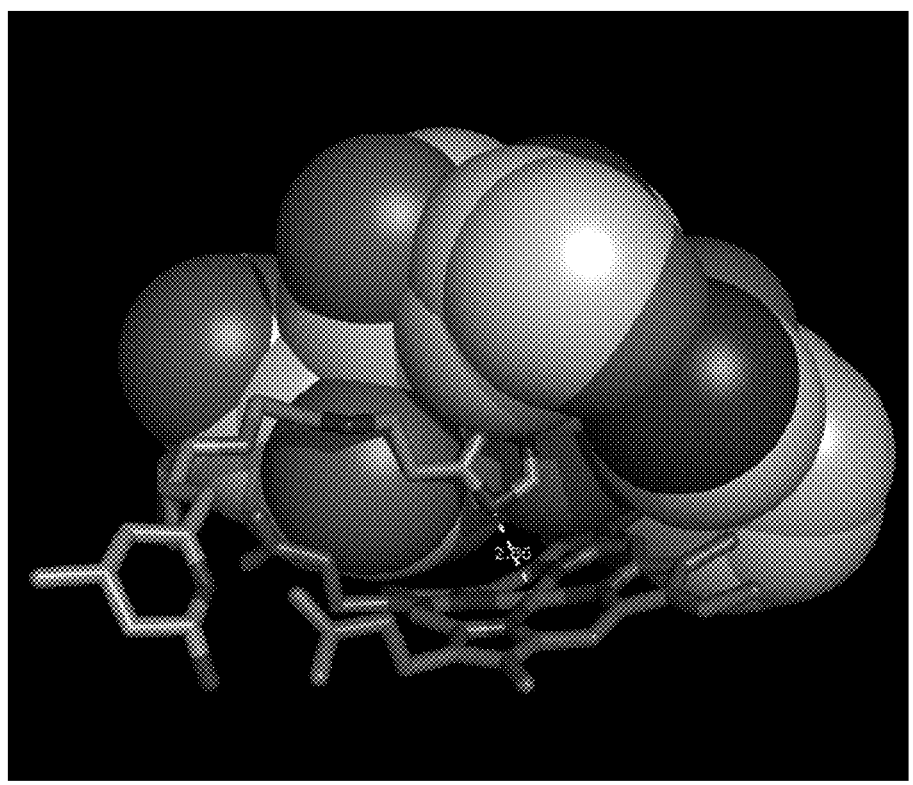
FIG. 2. Modified compound 2 from nNOS/compound 2 co-crystal structure (chain A) depicted with heme and all residues within 5 Angstroms of imidazole except V567, which is removed for clarity. Active site residues are depicted with doubled van der Waals radius to show ligand contact.

The distance from the imine nitrogen of the imidazole to the iron atom is 2.86 Angstroms in this simulation, but the heme ring in the crystal structure examined is clearly non-planar. (See, FIG. 2.) As the compound is simulated, it displaced the axial water ligand but did not coordinate to the iron, leading to a distortion caused by pentacoordination. However, it was believed that, with iron coordination, the heme ring will return to planarity and the distance will be shorter than that predicted by calculating only modification and energy minimization of an existing crystal structure.

From the many compounds known to efficiently bind heme, it is understood that five-membered azole rings, such as imidazole and 1,2,4-triazole, are particularly effective. (Correia, M. A.; Ortiz de Montellano, P. R Inhibition of Cytochrome P450 Enzymes. *In Cytochrome P450: Structure, Mechanism, and Biochemistry*, Ortiz de Montellano, P. R., Ed. Kluwer Academic/Plenum Publishers: New York, 2005; p 249.) Based on this observation, a series of analogs can be prepared, with various five-membered azole rings substituted for the 3-fluorophenyl ring of compound 2. For example, compounds 3a-h and 4a-h are synthesized, respectively, by preparing a common diastereomeric precursor then appending an azolylethylamine side chain using chemistry known in the literature. (See, e.g., Ji, H.; Stanton, B. Z.; Igarashi, J.; Li, H.; Martsek, P.; Roman, L. J.; Poulos, T. L.; Silverman, R. B. Minimal Pharmacophoric Elements and Fragment Hopping, and Approach Directed at Molecular Diversity and Isozyme Selectivity. Design of Selective Neuronal Nitric Oxide Synthase Inhibitors. *J. Am. Chem. Soc.* 2008, 130, 3900-3914, incorporated herein by reference in its entirety.) Following attachment of the side chain (e.g., using reductive amination), one deprotection step results in the target compound. With reference to Scheme 1, the present invention provides an efficient and straightforward route to a wide range of analog compounds from a common precursor.

Scheme 1

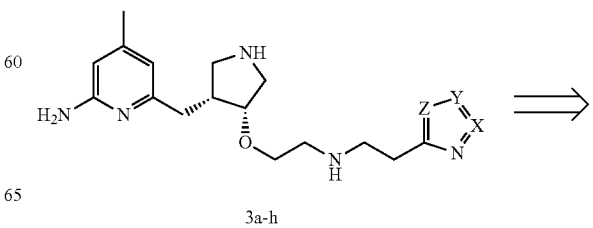

3a-h

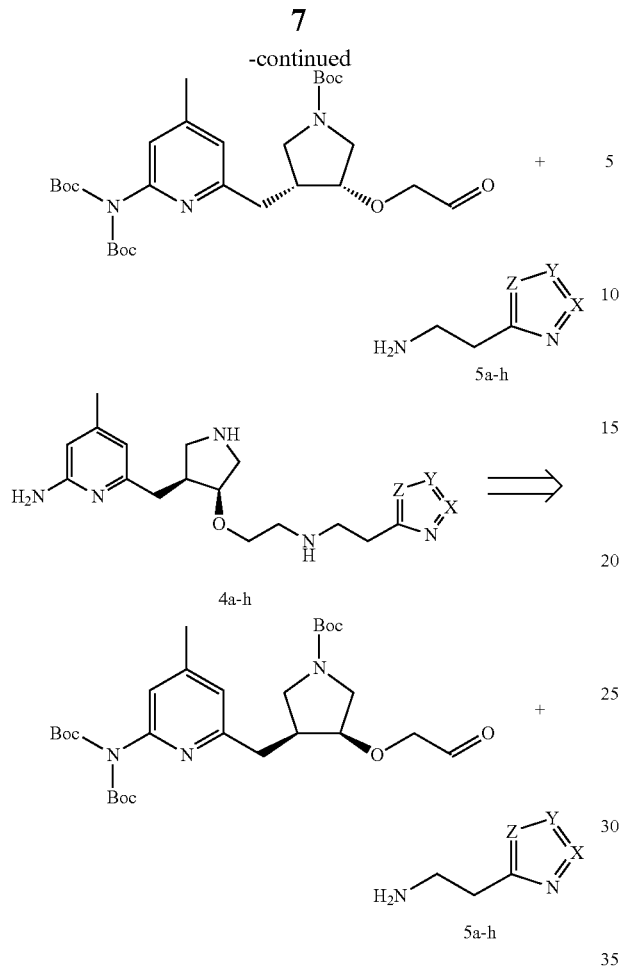

As would be understood in the art, many different ring substituents are possible with various points of connectivity and different combinations of heteroatoms. Changing heteroatoms and heteroatom ring positions produces a wide range of properties. For example, the $pK_a$ values of the imine nitrogen atom of the different azole rings—whether known in the scientific literature or as can be determined through techniques understood in the art—span a range of approximately 10 orders of magnitude. (See, e.g., Joule, J. A.; Mills, K. *Heterocyclic Chemistry*. 4 ed.; Blackwell Science Ltd.: Oxford, 2000.) (See, e.g., Table 1)

TABLE 1

Five-membered azole ring side chains and $pK_a$ values of free azole rings

| sidechain | structure | approximate ring $pK_a$ |
|---|---|---|
| 5a | H$_2$N~~~NH (imidazole) | 7.1 |
| 5b | H$_2$N~~~(imidazol-2-yl) | 7.1 |
| 5c | H$_2$N~~~(thiazol-2-yl) | 2.5 |
| 5d | H$_2$N~~~Cl-imidazole-NH | <7.1 |
| 5e | H$_2$N~~~(N-imidazolyl) | >7.1 |
| 5f | H$_2$N~~~(N-methylimidazole) | >7.1 |
| 5g | H$_2$N~~~(1-methylimidazol-4-yl) | >7.1 |
| 5h | H$_2$N~~~(1,2,4-triazol-3-yl) | 2.2 |

By using different heterocyclic rings, chemical and physiological properties can be modified and surveyed efficiently. For instance, rings containing different heteroatoms allow tuning of metal coordination. Additionally, choosing rings with different $pK_a$ values makes it possible to tune the charge state of the compound, which has implications for membrane permeability. For example, at physiological pH, a ring substituent with a $pK_a$ value of 5.4 would be essentially a free amine, but with a $pK_a$ value of 7.4 would be about half protonated. The latter sort of modification impacts physiological effect since increasing overall charge makes it less likely that such a compound will cross the blood-brain barrier (BBB).

A synthetic strategy involves attachment of various rings to ethylamine via organometallic-aziridine coupling, through known literature techniques, to provide the corresponding ethylamine-substituted ring intermediate. (See, e.g., Bergmeier, S. C.; Stanchina, D. M. Synthesis of Vicinal Amino Alcohols via a Tandem Acylnitrene Aziridination-Aziridine Ring Opening *J. Org. Chem.* 1997, 62, 4449-4456, incorporated herein by reference in its entirety.) Accordingly, aziridine can be prepared in good yield and coupled to a wide range of organometallic ring species, as shown in the preparation of intermediate 2-(imidazol-2-yl)ethylamine (5b) in Scheme 2. Various other azolyl-substituted ethylamine intermediates (e.g., without limitation, those listed in Table 1, above) can be prepared, analogously, such intermediates limited only by azolyl (e.g., thiazolyl, oxazolyl, etc.) starting material and availability of the corresponding organometallic ring species.

Scheme 2

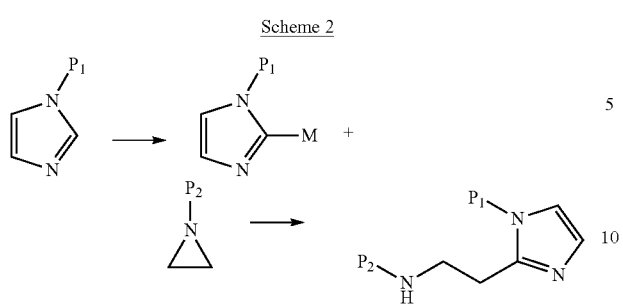

For some of the resulting azolylethylamines, regioisomers are possible, providing alternative ring orientations with respect to the ethylamine linker moiety. For example, for 1,3-oxazole the ethylamine side chain could be connected at the C-2, C-4 or C-5 positions depending on the organometallic starting material. The acidity associated with different carbon protons on the ring varies. By an in situ protection strategy similar to that previously reported, various carbons can be deprotonated sequentially, making it possible to obtain the various azolyl isomers for the side chain attachment. (Kraus, J. M.; Verlinde, C. L. M. J.; Karimi, M.; Lepesheva, G. I.; Gelb, M. H.; Buckner, F. S. Rational Modification of a Candidate Cancer Drug for Use Against Chagas Disease. *J. Med. Chem.* 2009, 52, 1639-1647, incorporated herein by reference in its entirety.) After synthesizing the first series of analogs, a series of the isomers can be prepared, using readily available reagents and starting materials, to probe which isomer can yield the most productive coordination. For example, with reference to compound 3a, the precursor azolylethylamine 5a is a known compound, histamine, which is commercially available.

With reference to Scheme 1, synthesis of an aldehyde precursor can begin with a Boc-protected 2-amino-4,6-dimethylpyridine and treatment with two equivalents of n-BuLi. The resulting dianion is allowed to react with a Boc-protected pyrrolidine epoxide to generate the corresponding trans-alcohol. (See, e.g., Schemes IIIb and I' in conjunction with examples 18-30 and 51-74, respectively, of the aforementioned incorporated '790 patent and/or '283 co-pending application.) The resulting pyrrolidine hydroxyl group is protected with tert-butyldimethylsilyl chloride (TBSCl) in the presence of imidazole to give the silyl ether. The free NH group on the pyridine ring can be further protected with another Boc-protecting group using (Boc)$_2$O in the presence of 4-dimethylaminopyridine (DMAP). The silyl ether can then be cleaved using tetrabutylammonium fluoride (TBAF) to provide the tri-Boc protected pyrrolidine alcohol. The two enantiomers are resolved through camphanic ester derivatives using a Mitsunobu reaction to generate the two separable (3R,4R) and (3S,4S) diastereomers. The ester linkage of the desired diastereomer is hydrolyzed using Na$_2$CO$_3$ to provide chiral hydroxypyrrolidine precursors.

The cis chiral alcohols are separately treated with 0.025 equivalents of palladium tetrakistriphenylphosphine under argon atmosphere, and heated to reflux in THF, at which time, allyl-t-butylcarbonate is added. The mixture is allowed to react for 3 hours. The resulting alkene is subjected to ozonolysis using Me$_2$S as reducing reagent to generate the corresponding aldehyde, which is reductively aminated with an azolylethylamine of the sort discussed above (e.g., 5a-h) using NaHB(OAc)$_3$ to generate the cis-diastereomers. Finally, the three Boc-protecting groups can be removed concurrently in HCl to generate inhibitors 3a-h or 4a-h.

Compounds 3a (not shown, below), 4a, 3c, and 4c were synthesized compounds for purpose of illustration, and 4a, 3c and 4c have been tested using literature protocols. (See, e.g., example 51 of the aforementioned incorporated '790 patent, example 12 of co-pending application Ser. No. 13/250,554 filed Sep. 30, 2011, also incorporated herein by reference in its entirety and, respectively, the references cited therein.) The activities are shown in Table 2.

TABLE 2

K$_I$ values and ratios (i.e., selectivity) for representative compounds

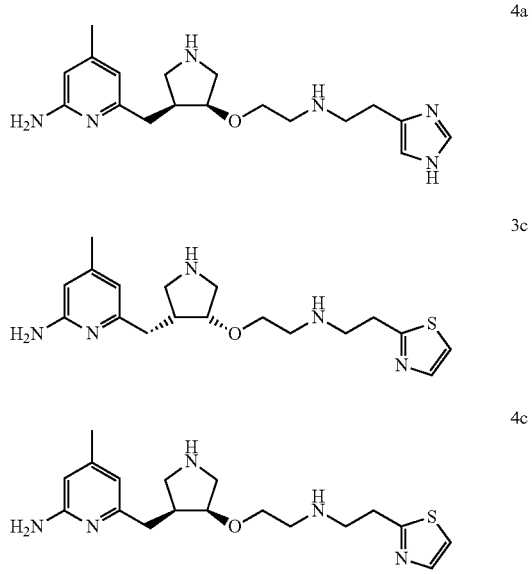

| Compound | K$_I$ (μM) | | | selectivity | |
| --- | --- | --- | --- | --- | --- |
| | nNOS | iNOS | eNOS | i/n | e/n |
| 4a | 1.18 | 15.0 | 4.23 | 12.7 | 3.58 |
| 3c | 0.716 | 23.1 | 0.058 | 32.3 | 0.081 |
| 4c | 0.044 | 34.4 | 9.81 | 782 | 223 |

As can be seen in Table 2, imidazoles 4a and 4c provide moderate potency. Thiazole 3c, however, is highly potent. Such was the intended effect of the analogs with (3R,4R) stereochemistry, based on the theory that the azole ring can coordinate to the heme ring. The fact that two (3S,4S) compounds are not as potent is consistent with model predictions. The (3S,4S) stereochemistry is expected to bind with the imidazole away from the heme at the opposite side of the binding site, which is not as favorable.

While the principles of this invention have been described in connection with specific embodiments, it should be understood clearly that these descriptions are added only by way of example and are not intended to limit, in any way, the scope of this invention. While the utility of this invention is illustrated through the use of several compounds and azolyl moieties thereof, it will be understood by those skilled in the art that comparable results are obtainable with various other compounds and moieties, as are commensurate with the scope of this invention. Other advantages and features will become apparent from the claims hereinafter, with the scope of such claims determined by the reasonable equivalents, as understood by those skilled in the art.

We claim:

1. A compound selected from compounds of a formula

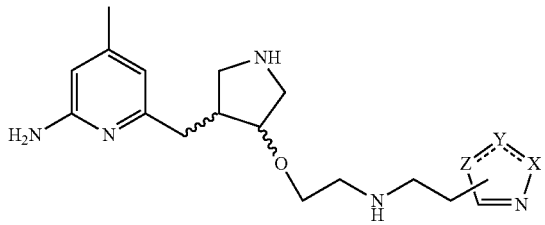

wherein X, Y and Z are independently selected from CR$_1$, CH$_2$, O, S, N and NR$_2$ moieties; each said R$_1$ is independently selected form H, alkyl and halo moieties and a covalent bond to said ethanamine moiety; and each said R$_2$ is independently selected from H and alkyl moieties; and salts thereof.

2. The compound of claim 1 wherein one of X, Y, and Z is a heteroatom moiety.

3. The compound of claim 2 wherein each of X and Z is CH, and Y is NH, said compound comprising an imidazolyl moiety.

4. The compound of claim 2 wherein each of X and Y is CH, and Z is S, said compound comprising a thiazolyl moiety.

5. The compound of claim 1 comprising a cis diastereomeric configuration.

6. The compound of claim 1 wherein said compound is an ammonium salt.

7. The compound of claim 6 wherein said ammonium salt has a counter ion that is a conjugate base of a protic acid.

8. The compound of claim 1 contacting a nitric oxide synthase.

9. The compound of claim 8 in a configuration for heme coordination of said azolyl moiety.

10. A compound selected from compounds of a formula

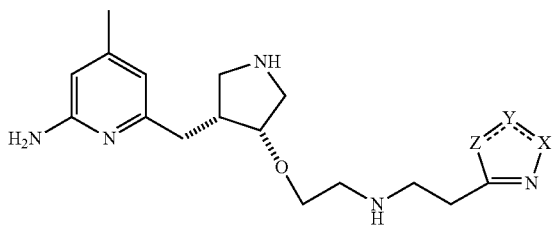

wherein X, Y and Z are independently selected from CR$_1$, CH$_2$, O, S, N and NR$_2$ moieties; each said R$_1$ is selected from H and alkyl moieties; and each said R$_2$ is independently selected from H and alkyl moieties; and salts thereof.

11. The compound of claim 10 wherein said azolyl moiety is selected from imidazol-4-yl and thiazol-2-yl moieties.

12. The compound of claim 11 wherein said compound is an ammonium salt, and said salt has a counter ion that is a conjugate base of a protic acid.

13. A method of using azolyl basicity to affect bioavailability of a nitric oxide synthase inhibitor compound, said method comprising:
providing a compound of claim 1, said compound comprising an azolyl moiety with an imine nitrogen substantially unprotonated at physiological pH; and
contacting said compound with a lipophilic medium.

14. The method of claim 13 wherein said azolyl moiety has a pK$_a$ value ≤ about 5.4.

15. The method of claim 13 wherein said medium models one of a cellular membrane and the brain blood barrier.

16. A method of inhibiting a nitric oxide synthase comprising contacting a nitric oxide synthase with an effective amount of a compound of a formula

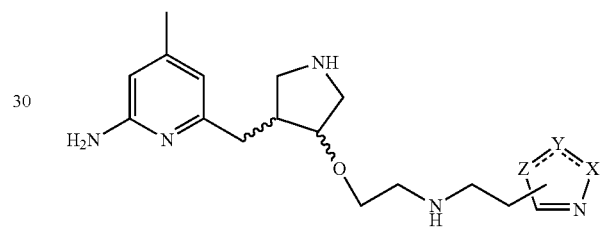

wherein X, Y and Z are independently selected from CRi, CH$_2$, O, S, N and NR$_2$ moieties; each said R$_1$ is selected from H and alkyl moieties; and each said R$_2$ is independently selected from H and alkyl moieties; and salts thereof.

17. The method of claim 16 wherein said azolyl moiety is selected from imidazolyl and thiazolyl moieties.

18. The method of claim 17 wherein said compound is selected from (S,S) and (R,R) enantiomers.

19. The method of claim 18 wherein said compound is the (R,R) enantiomer, said method selective for inhibition of neuronal nitric oxide synthase.

* * * * *

UNITED STATES PATENT AND TRADEMARK OFFICE
CERTIFICATE OF CORRECTION

PATENT NO. : 8,618,143 B1
APPLICATION NO. : 13/275748
DATED : December 31, 2013
INVENTOR(S) : Richard B. Silverman and James M. Kraus It is certified that error appears in the above-identified patent and that said Letters Patent is hereby corrected as shown below:

In the specification:
Column 8, lines 7-13
Replace the structure for 5d in Table 1 as printed with the structure for 5d in the Request in order to correct an error in the structure as follows:

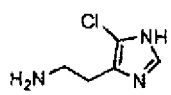

In the claims:
Column 12, line 37
"wherein X, Y and Z are independently selected from CRi," should be --wherein X, Y and Z are independently selected from $CR_1$,--.

Column 12, line 43
"The method of claim 17 where said compound is" should be --The method of claim 16 wherein said compound is--.

Signed and Sealed this
Seventeenth Day of June, 2014

Michelle K. Lee
*Deputy Director of the United States Patent and Trademark Office*

UNITED STATES PATENT AND TRADEMARK OFFICE
CERTIFICATE OF CORRECTION

| | | |
|---|---|---|
| PATENT NO. | : 8,618,143 B1 | Page 1 of 1 |
| APPLICATION NO. | : 13/275748 | |
| DATED | : December 31, 2013 | |
| INVENTOR(S) | : Richard B. Silverman et al. | |

It is certified that error appears in the above-identified patent and that said Letters Patent is hereby corrected as shown below:

In the Specification:

Column 1, after line 7
Please insert --This invention was made with government support under grant number GM049725 awarded by the National Institutes of Health. The government has certain rights in the invention--

Signed and Sealed this
Twenty-first Day of April, 2015

Michelle K. Lee
*Director of the United States Patent and Trademark Office*